(12) United States Patent
Iyer

(10) Patent No.: US 7,725,177 B2
(45) Date of Patent: May 25, 2010

(54) FILTERED FEEDTHROUGH ASSEMBLIES FOR IMPLANTABLE MEDICAL DEVICES AND METHODS OF MANUFACTURE

(75) Inventor: Rajesh V. Iyer, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 511 days.

(21) Appl. No.: 11/846,930

(22) Filed: Aug. 29, 2007

(65) Prior Publication Data
US 2009/0059468 A1 Mar. 5, 2009

(51) Int. Cl.
*A61N 1/00* (2006.01)
(52) U.S. Cl. .......................................... 607/2
(58) Field of Classification Search ................ 607/2, 607/37; 429/181; 361/302, 517
See application file for complete search history.

(56) References Cited

U.S. PATENT DOCUMENTS

| | | | |
|---|---|---|---|
| 6,212,063 B1 | 4/2001 | Johnson et al. | |
| 6,275,369 B1 | 8/2001 | Stevenson et al. | |
| 6,349,025 B1* | 2/2002 | Fraley et al. | 361/302 |
| 6,768,629 B1 | 7/2004 | Allen et al. | |
| 7,035,077 B2 | 4/2006 | Brendel | |
| 7,038,900 B2 | 5/2006 | Stevenson et al. | |
| 2003/0179536 A1* | 9/2003 | Stevenson et al. | 361/302 |
| 2004/0258988 A1 | 12/2004 | Nielsen et al. | |
| 2007/0179553 A1 | 8/2007 | Iyer et al. | |

FOREIGN PATENT DOCUMENTS

| | | |
|---|---|---|
| DE | 10059373 A1 | 7/2001 |
| WO | WO03073450 A | 9/2003 |

OTHER PUBLICATIONS

Stevenson et al, Feedthrough EMI Filter with Ground Isolation for Cardiac Pacemakers and Implantable Cardioverter Defibrillators, Engineering in Medicine and Biology Society, 1998. Proceedings of the 20th Annual International conference of athe IEEE Hong Kong, China Oct. 29-Nov. 1, 1998, Piscataway, NJ, USA, IEEE, US, vol. 6, (Oct. 29, 1998), pp. 3319-3323.
International Search Report-PCT/US2008/074739, Apr. 12, 2008, 7 pages.
Iyer, Rajesh, US Patent Application entitled, "Filtered Feedthrough Assembly and Method of Manufacture", filed Dec. 29, 2005, and identified as U.S. Appl. No. 11/321,382.

* cited by examiner

*Primary Examiner*—George Manuel
*Assistant Examiner*—Robert N Wieland

(57) ABSTRACT

A feedthrough assembly for an implantable medical device includes an insulator element hermetically sealed to a ferrule and a feedthrough member, and a capacitive element spaced apart from the insulator element within the ferrule and coupled to the feedthrough member by a conductive material; the conductive material extends in an area between the capacitive element and the feedthrough member. The assembly further includes a heat and pressure deformed thermoplastic adhesive member that extends around the feedthrough member within the ferrule, is located between the capacitive element and the insulator element, and is sealed to an external surface of the capacitive element in order to isolate the conductive material.

20 Claims, 7 Drawing Sheets

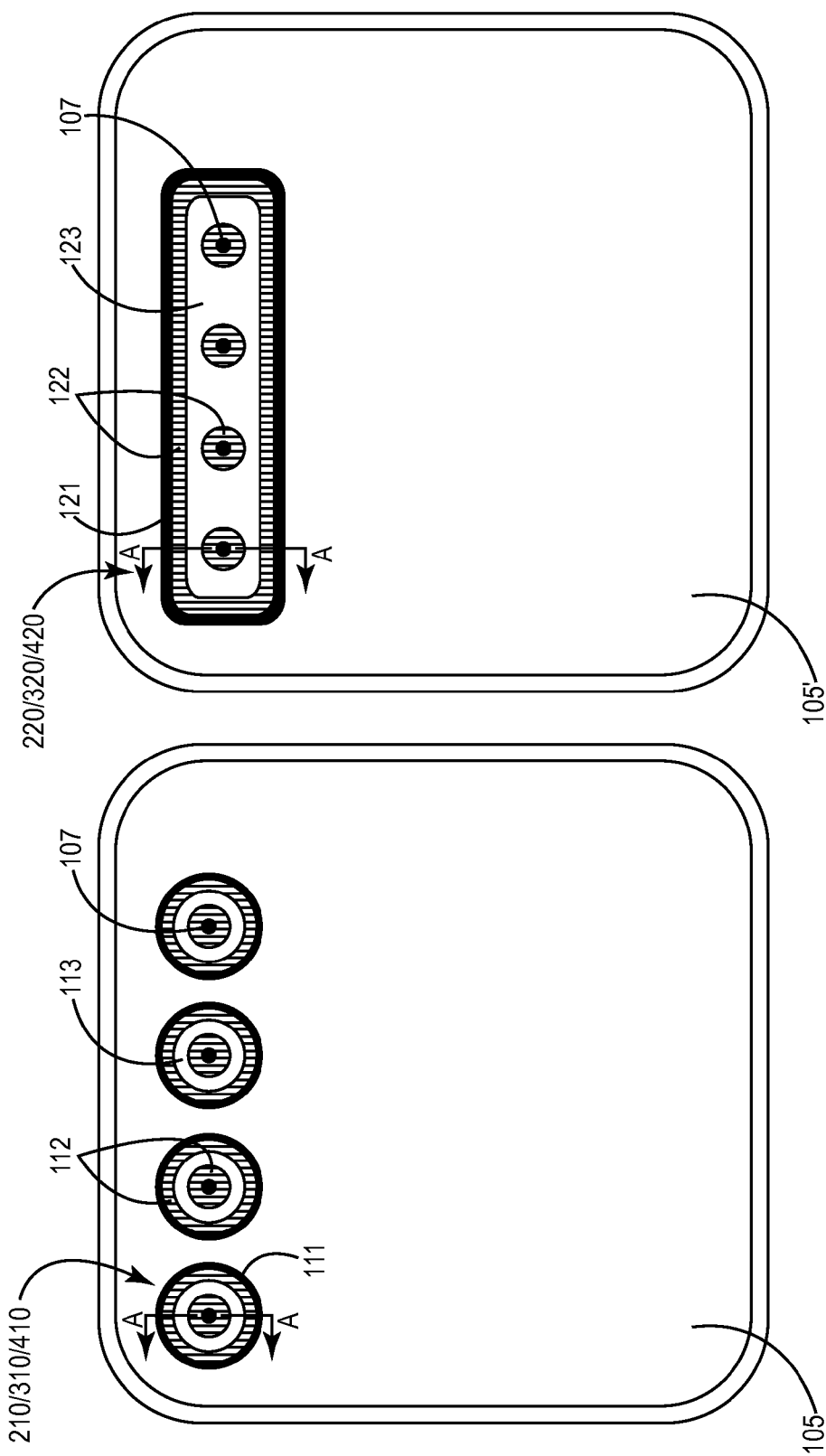

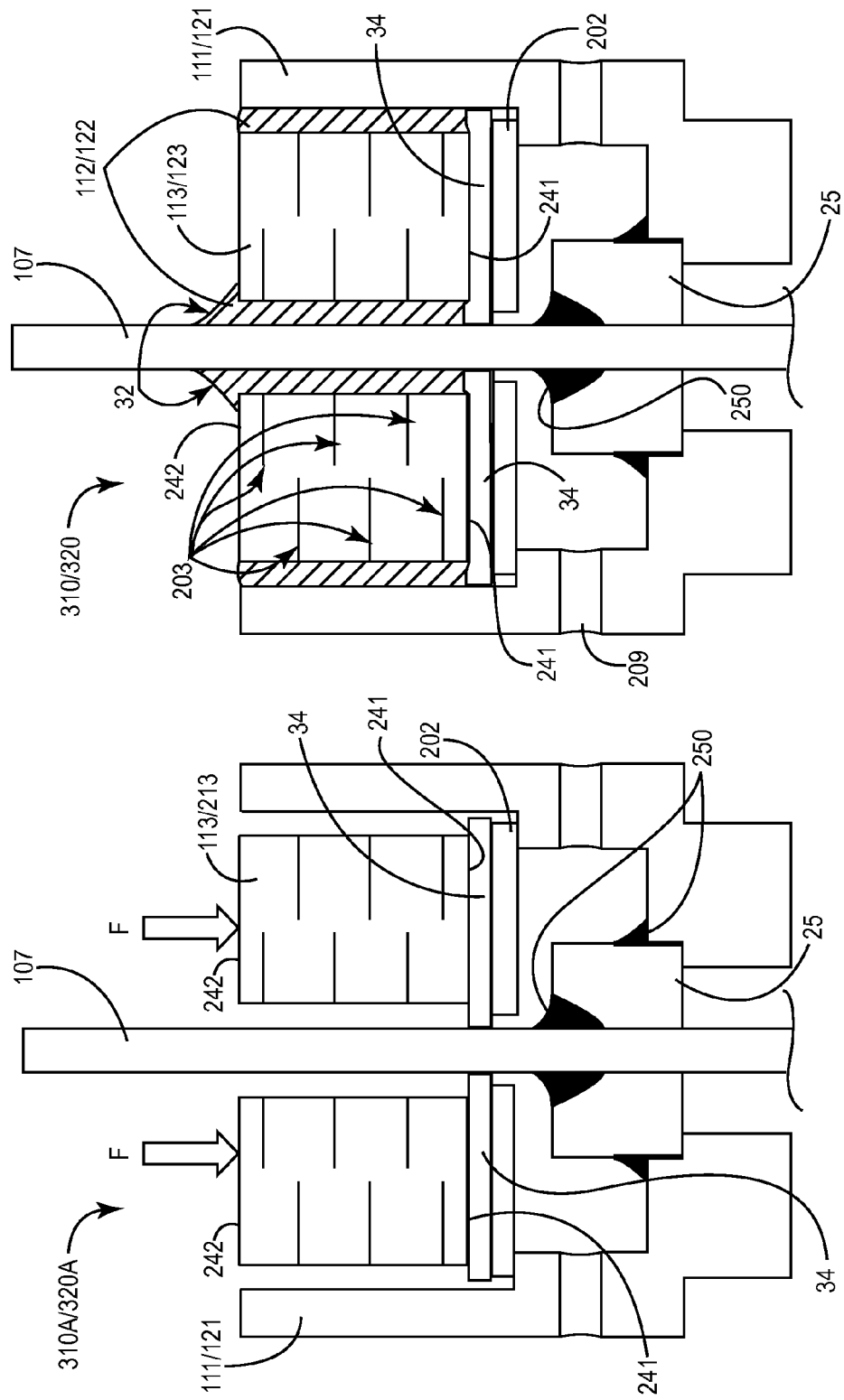

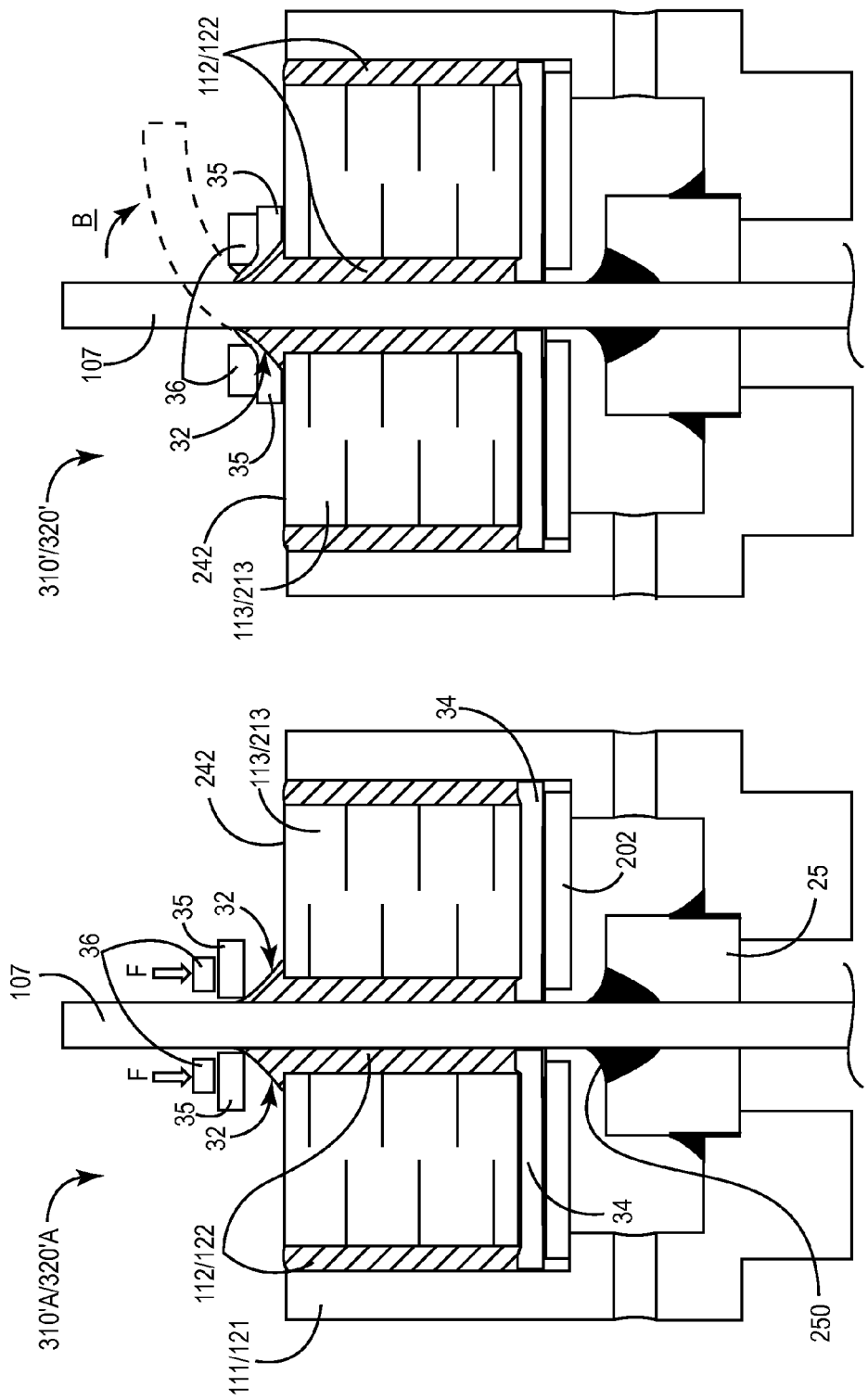

FILTERED FEEDTHROUGH ASSEMBLIES FOR IMPLANTABLE MEDICAL DEVICES AND METHODS OF MANUFACTURE

TECHNICAL FIELD

The present invention pertains to implantable medical devices and more particularly to filtered feedthrough assemblies employed by the devices.

BACKGROUND

Implantable medical devices (IMD's), for example, cardiac pacemakers, defibrillators, neurostimulators and drug pumps, which include electronic circuitry and battery elements, require a housing to contain and hermetically seal these elements within a body of a patient. Many of these IMD's include one or more electrical feedthrough assemblies to provide electrical connection between the elements contained within the housing and components of the IMD external to the housing, for example, sensors and/or electrodes and/or lead wires mounted on an exterior surface of the housing, or electrical contacts housed within a connector module, which is mounted on the housing to provide coupling for lead wires.

A feedthrough assembly for an IMD can be unipolar or multipolar (e.g. bipolar etc.). A unipolar feedthrough assembly includes a single feedthrough member, or pin, that extends from an interior to an exterior of the housing through a ferrule, while a multipolar feedthrough assembly includes a plurality of such feedthrough members extending through a single ferrule. In each type of assembly, the feedthrough pin(s) is/are electrically isolated from the ferrule, and, in the case of the multipolar assembly, from one another, by an insulator element, for example, glass or ceramic, that is mounted within the ferrule and surrounds the feedthrough pin(s). The insulator is hermetically sealed to the ferrule and to the feedthrough pin(s), typically, by a braze joint.

To reduce the effects of stray electromagnetic interference (EMI) signals that may be collected by lead wires electrically coupled to the feedthrough pins, it is known to incorporate, within feedthrough assemblies, capacitive elements for high frequency filtering. A filtered feedthrough assembly may be formed by mounting the capacitive element within the ferrule after sealing the insulator element to the ferrule and the feedthrough pin(s); the capacitive element typically includes an insulative base, for example, a ceramic monolith, in which electrode plates are embedded, otherwise known as a discoidal-type capacitor. A first set of the electrode plates are electrically coupled to a conductive layer overlaying an inner surface of the capacitive element, and a second set of the electrode plates are electrically coupled to another conductive layer overlaying an outer surface of the capacitive element. Typically, a conductive material applied between the inner surface of the capacitive element and the pin, and between the outer surface of the capacitive element and the ferrule, forms an electrical coupling between the first set of electrode plates and the pin, and between the second set of electrode plates and the ferrule.

There is a need in filtered feedthrough assemblies, such as those described above, to isolate, within the ferrule, the conductive material, which forms the electrical couplings of the capacitive element, from the brazed joints of the insulator element. In the past this need has been met by applying an insulative barrier of a non-conductive thermosetting adhesive, between the capacitive element and the insulator element, prior to applying the conductive material. However, this approach requires careful control of adhesive volumes in order to prevent excess adhesive from wicking into those areas between the ferrule and the capacitive element, and between the feedthrough pin and the capacitive element, where a presence of subsequently applied conductive material is intended. Thus, in order to provide for this isolation, while simplifying the assembly process, there is a need for new isolation methods and materials.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 1B is a plan view of a portion of the IMD shown in FIG. 1A including a plurality of unipolar filtered feedthrough assemblies, according to some embodiments of the present invention.

FIG. 1C is a plan view of a portion of the IMD shown in FIG. 1A including a multi-polar filtered feedthrough assembly, according to some other embodiments of the present invention.

FIG. 3A is a section view, per section line A-A of FIGS. 1A-B, of a partially formed feedthrough assembly, according to some embodiments of the present invention.

FIG. 3B is a section view through section line A-A of FIGS. 1A-B of a feedthrough assembly formed from the partially formed assembly shown in FIG. 3A, according to some embodiments of the present invention.

FIG. 3C is a section view, per section line A-A of FIGS. 1A-B, of another partially formed feedthrough assembly, according to further embodiments of the present invention.

FIG. 3D is a section view, per section line A-A of FIGS. 1A-B, of a feedthrough assembly formed from the partially formed assembly shown in FIG. 3C, according to further embodiments of the present invention.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

One embodiment of the present invention relates to connecting or attaching at least one or more capacitors in a filtered feedthrough using thermoplastic adhesives. In one embodiment, the method described hereunder prevents wicking of non-conductive epoxy in the capacitor inner diameter (ID). Additionally, undesired flow of the epoxy into the brazed joint is prevented. One embodiment of the proposed method for capacitor attachment utilizes thermoplastic adhesive film (e.g. polysulphone, phenoxy, urethane etc.). This film is typically in the form of a washer that is placed through a feedthrough pin. At least one or more capacitors is then placed over the thermoplastic film. Adequate weights are then placed on the capacitor. The resultant assembly is then placed inside a batch oven or in-line belt furnace at temperatures ranging from about 100° Celcius (C) to about 375° C. that forms a good seal under the capacitor. Since thermoplastic adhesives have no flow, no undesired wicking into the capacitor ID or into the brazed/glassed joint of the feedthrough is experienced.

Figure 1A:
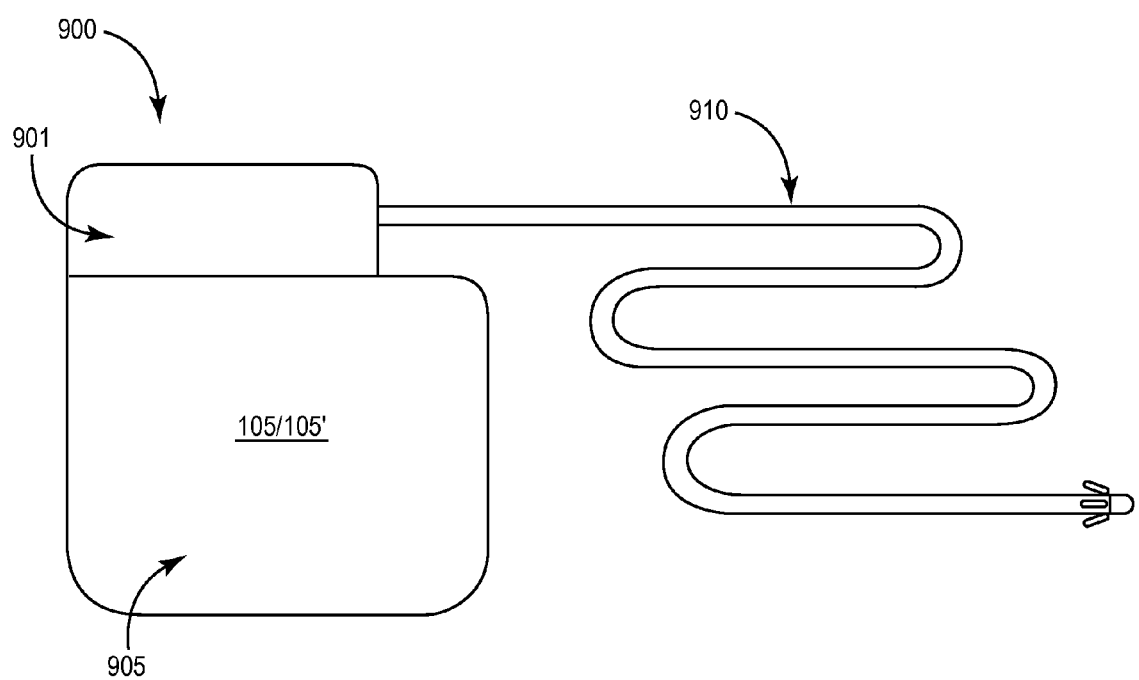
FIG. 1A is a plan view of an IMD system, according to exemplary embodiments of the present invention.

FIG. 1A is a plan view of an IMD system, according to exemplary embodiments of the present invention. FIG. 1A illustrates the system including a stimulation source, or device 900, coupled to a medical electrical lead 910 via coupling of a connector end (not shown) of lead 910 to electrical contacts (not shown) within a header block 901 of device 900. FIG. 1A further illustrates device 900 including a can, or housing 905 to which header block 901 is attached. Those skilled in the art will appreciate that hermetically sealed feedthrough members, or pins, extend through a sidewall 105/105' of housing 905 in order to electrically couple the contacts, within header block 901, to electronic circuitry enclosed within housing 905.

Figure 1D:
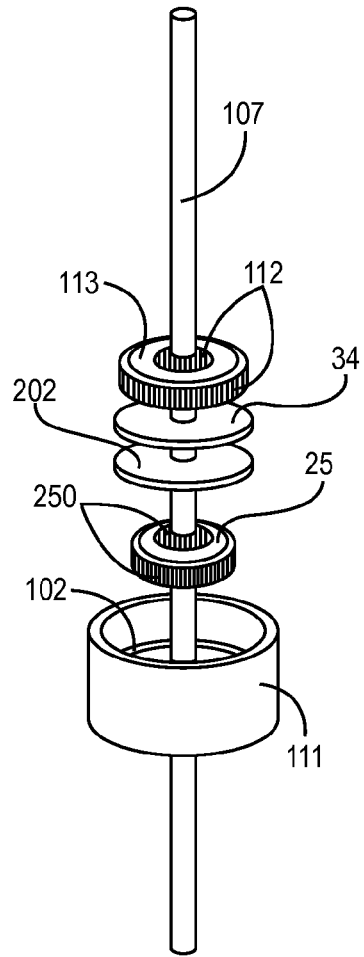
FIGS. 1D-E are exploded perspective views of feedthrough assemblies corresponding to FIGS. 1B-C, respectively, according to some embodiments of the present invention.
Figure 1E:
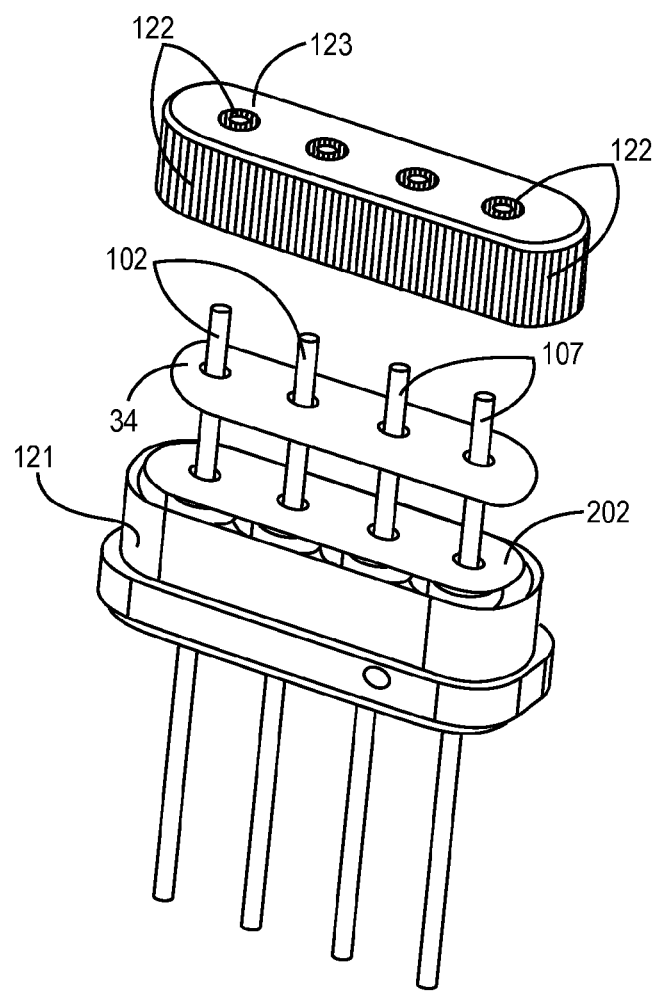
Figure 2:
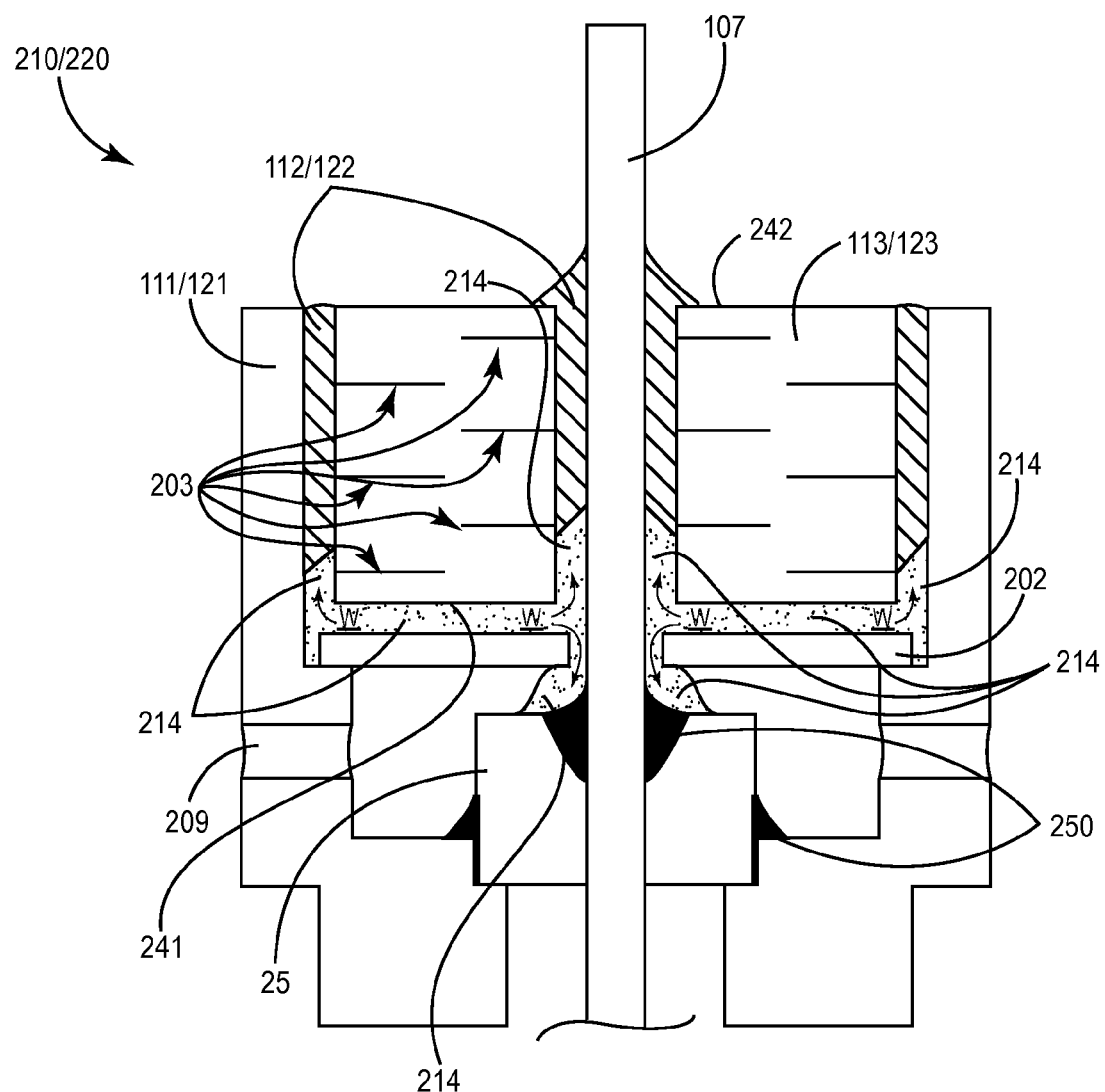
FIG. 2 is a section view through section line A-A of FIGS. 1A-B, according to a prior art embodiment.
Figure 4:
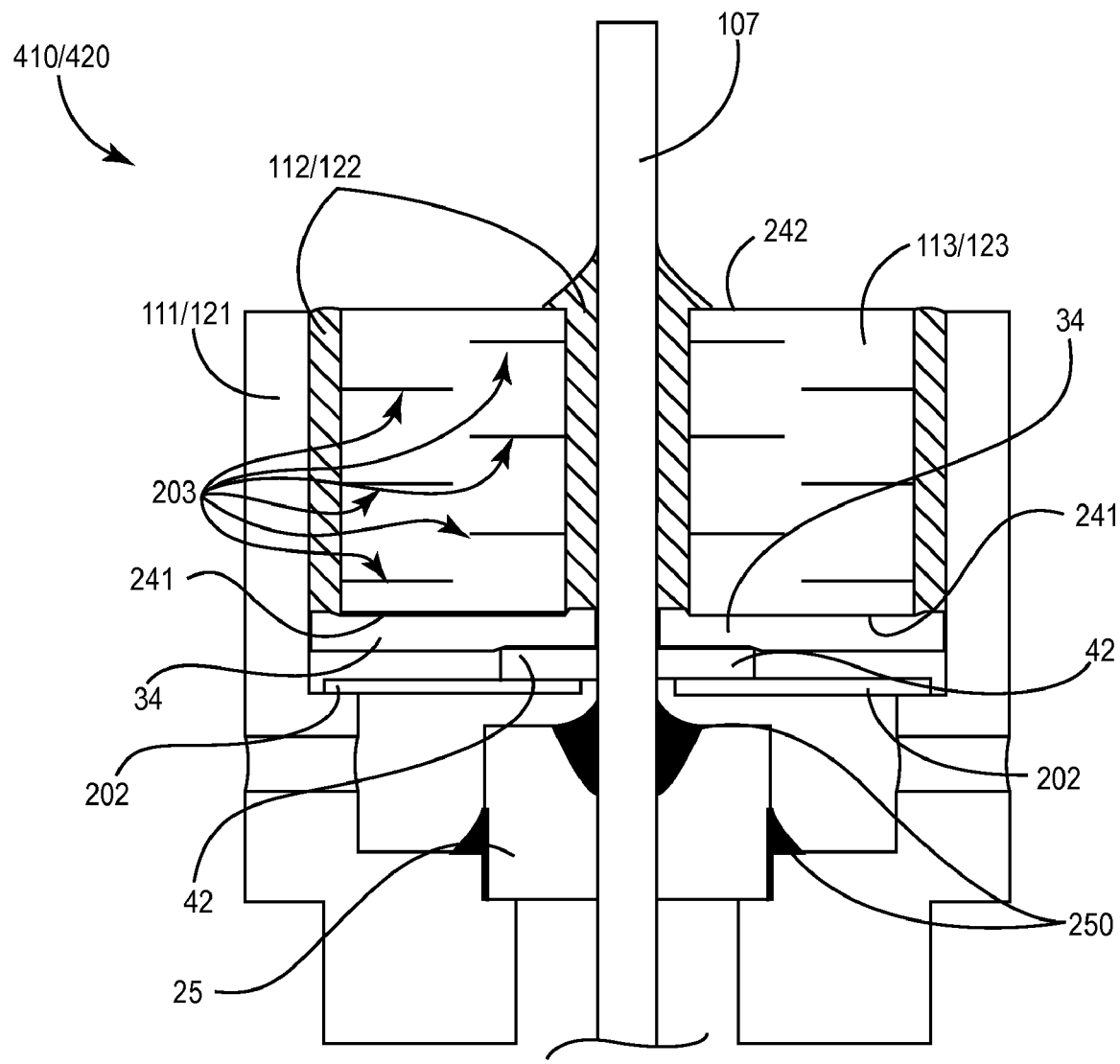
FIG. 4 is a section view through section line A-A of FIGS. 1A-B of yet another feedthrough assembly, according to additional embodiments of the present invention.

FIGS. 1B-C are plan views of a portion of the IMD shown in FIG. 1A, according to alternate groups of embodiments; and FIGS. 1D-E are exploded perspective views of feedthrough assemblies 310, 320 corresponding to FIGS. 1B-C, respectively, according to some embodiments of the present invention. FIG. 1B illustrates four unipolar feedthrough assemblies 210/310/410 mounted in housing sidewall 105 and each unipolar assembly 210/310/410 including a feedthrough member, or pin 107, extending through a ferrule 111, which is joined, for example, via welding, to sidewall 105. FIG. 1B shows an interior side of housing sidewall 105, so that capacitive elements 113 can be seen surrounding each pin 107 within each ferrule 111. With reference to FIG. 1D, which is an exploded view of assembly 310, and to FIGS. 2, 3B and 4, which are section views through section line A-A of FIG. 1B, each assembly 210 (FIG. 2), 310 (FIGS. 1D and 3B), and 410 (FIG. 4) also includes an insulator element 25 surrounding pin 107 to electrically isolate pin 107 from ferrule 111. FIG. 1C illustrates a multipolar feedthrough assembly 220/320/420, wherein a single ferrule 121, which is joined to housing sidewall 105', surrounds a single capacitive element 123, which in turn surrounds four of pins 107, according to a second group of embodiments. Like FIG. 1B, FIG. 1C includes section line A-A, and also shows an interior side of housing sidewall 105'. The exploded view of assembly 320, in FIG. 1E, and the section views of FIGS. 2, 3B, and 4 are representative of various multipolar feedthrough assemblies 220 (FIG. 2), 320 (FIGS. 1E and 3B), and 420 (FIG. 4). Suitable materials for feedthrough members 107 and ferrule 111/121 include, without limitation, titanium, niobium, platinum, platinum/iridium, molybdenum, zirconium and tantalum. It should be noted that any embodiments (e.g. unipolar, multipolar etc.), insulator element 25, for example glass or ceramic, may include discrete/individual elements, each one surrounding a corresponding feedthrough member 107, or be a single element, surrounding all feedthrough members 107. It should also be noted that embodiments of the present invention are not limited by any particular number of feedthrough assemblies or feedthrough members/pins 107.

FIGS. 1B-E further illustrate a conductive material 112/122 located between each feedthrough member 107 and the corresponding capacitive element 113/123, and between capacitive element(s) 113/123 and ferrule(s) 111/121. Turning now to FIG. 2, capacitive elements 113/123 may be seen to include a plurality of spaced apart electrode disks, or plates 203, wherein a first set of plates 203 is located adjacent an outer surface of element 113/123 for electrical coupling, via conductive material 112/122, to ferrule 111/121, and a second set of plates 203 is located adjacent to an inner surface of element 113/123 for electrical coupling, via conductive material 112/122, to pin 107. Those skilled in the art will recognize that plurality of disks/plates 203 embedded within an insulative monolith, for example, ceramic, of capacitive element(s) 113/123 forms a discoidal-type capacitor for high frequency filtering of the corresponding feedthrough member 107. Those skilled in the art will further appreciate that the outer surface of capacitive element 113/123, adjacent the first set of electrode plates 203, and the inner surface of capacitive element 113/123, adjacent the second set of electrode plates, are typically overlaid with a layer of conductive material, for example, a silver-palladium termination material, to provide an electrical coupling surface between electrode plates 203 and conductive material 112/122.

FIG. 2 illustrates a non-conductive material 214, for example, a thermosetting epoxy adhesive, extending between hermetically sealing joints 250 of insulator element 25, for example, formed by a gold braze, and conductive material 112/122, in order to electrically isolate joints 250 from material 112/122. With further reference to FIG. 2, which is representative of a prior art embodiment, it may be appreciated that non-conductive material 214, which is typically applied and cured prior to an application of conductive material 112/122, has encroached via wicking per arrows W, into areas between ferrule 111/121 and capacitive element 113/123, and between feedthrough member 107 and capacitive element, 113/123 thereby limiting an extent of conductive material 112/122 for electrical coupling. This encroachment may cause an increase in a equivalent series resistance resulting in compromised high frequency filtering for assembly 210/220. FIG. 2 further illustrates non-conductive material 214 having wicked past a non-conductive divider 202 to cover joint 250 of insulator element that extends about feedthrough member 107; this encroachment of non-conductive material 214 can frustrate leak testing, for example, applied via a port 209 in ferrule 111/121, to verify the hermetic sealing capacity of joints 250. In order to avoid the illustrated wicking issue, without requiring painstaking control over application volumes and flow of non-conductive material 214, for example, the epoxy adhesive, embodiments of the present invention employ alternate electrical isolation methods and materials.

FIG. 3A is a section view, per section line A-A of FIGS. 1A-B, of a partially formed feedthrough assembly, or a subassembly 310A/320A, according to some embodiments of the present invention; and FIG. 3B is a section view through section line A-A of FIGS. 1A-B of a feedthrough assembly 310/320 formed from subassembly 310A/320A, according to some embodiments. FIG. 3A illustrates subassembly 310A/320A including insulator element 25, which is hermetically sealed to both feedthrough member 107 and to ferrule 111/121 by hermetically sealing joints 250, capacitive element 113/213, which is spaced apart from insulator element 25 by non-conductive divider 202, and a thermoplastic adhesive member 34, extending around feedthrough member 107, and between a first external surface 241 of capacitive element 113/123 and divider 202. The item numbers 310A and 310 denote a unipolar type, and 320A and 320, a multipolar type, with reference to FIGS. 1B and 1D, and to FIGS. 1C and 1E, respectively. According to the illustrated embodiment, divider 202, which may be formed from any suitable and fairly rigid non-conductive material, examples of which include, without limitation polyimide, alumina, polysulfone and polyether ether ketone (PEEK), is supported on an internal ledge 102 of ferrule 111/121; divider 202 supports adhesive member 34 and capacitive element 113/123 such that when a force is applied, per arrows F, to a second external surface 142 of capacitive element 113/123, and heat is applied in conjunction with the force, thermoplastic adhesive member 34 will deform to conform to first external surface 241 of capacitive element 113/123, for example, as illustrated in FIG. 3B. Member 34 is thus disposed to provide electrical isolation between joints 250 and conductive material 112/122, which material 112/122 is subsequently backfilled into areas between capacitive element 113/123 and ferrule 111/121 and between capacitive element 113/123 and feedthrough member 107. FIGS. 1D and 1E show preferred geometries of member 34 for unipolar assembly 310 and bipolar assembly 320, respectively.

Because of the nature of thermoplastic materials, thermoplastic adhesive member 34 deforms, under the applied heat and pressure, about surface 241 to form a seal, without wicking into the areas intended for conductive material 112/122, or onto joint 250 of insulator element 25, which surrounds feedthrough member 107. Member 34 may be formed from any suitable thermoplastic adhesive material, preferably, polysulfone, PEEK or phenoxy. The heat may be applied at a temperature in a range from approximately 100° C. to approximately 375° C., for example, within a batch oven or an in-line belt furnace, for a time ranging from approximately ten seconds to approximately three minutes (compared to times ranging from thirty minutes to two hours, for traditional thermosetting adhesives used in this application), and the force may be applied, by mounting a weighting member, for example, having a weight in a range from approximately 13 grams to approximately 130 grams, onto second external surface 242 of capacitive element 113/213.

With further reference to FIG. 3B, it may be appreciated that, because the deformation of adhesive member 34 does not cause member 34 to flow and thereby unnecessarily encroach into the areas around the inner and outer surfaces of capacitive element 113/123, a maximum amount of conductive material 112/122 may fill in the areas along the inner and outer surfaces of capacitive element 113/123 to maintain a minimum equivalent series resistance for uncompromised high frequency filtering performance. In addition, since the heat and pressure deformed thermoplastic adhesive member 34 does not flow to cover either of hermetically sealing joints 250, the leak testing of joints 250, via port 209, is not frustrated by creating the electrical isolation with adhesive member 34. Furthermore, maintaining a repeatable volume for backfilling of conductive material 112/122 allows for an automated dispensing of repeatable volumes of conductive material 112/122 from one feedthrough assembly to the next; examples of conductive material 112/122 include, without limitation, a conductive epoxy and a conductive polyimide, either silver or gold filled, formulated for syringe injection.

According to alternate methods of the present invention, thermoplastic adhesive member 34 is applied to surface 241 of capacitive element 113/123, via heat and pressure deformation, prior to assembling capacitive element 113/123 into ferrule 111/121. Thus, according to alternate embodiments, which are formed in this manner, divider 202 is not necessary, and deformed member 34 may rest directly against internal ledge 102 of ferrule 111/121.

FIG. 3C is a section view, per section line A-A of FIGS. 1A-B, of another partially formed feedthrough assembly, or subassembly 310'A/320'A, according to further embodiments of the present invention; and FIG. 3D is a section view, per section line A-A of FIGS. 1A-B, of a feedthrough assembly 310'/320' formed from subassembly 310'A/320'A, according to some embodiments. (The item numbers 310'A and 310' denote a unipolar type, and 320'A and 320', a multipolar type, for example, with reference to FIGS. 1B and 1D, and to FIGS. 1C and 1E, respectively.) FIG. 3C illustrates subassembly 310'A/320'A including insulator element 25, capacitive element 113/213, conductive material 111/121, and heat and pressure deformed thermoplastic adhesive member 34, similar to assembly 310/320 of FIG. 3B, wherein member 34 isolates conductive material 112/122 from joints 250 of insulator element 25. FIG. 3C further illustrates subassembly 310'A/320'A including another thermoplastic adhesive member 35 in the form of a washer mounted about feedthrough member 107 and over a fillet 32 of conductive material 112/122, which fillet 32 extends adjacent to second external surface 242 of capacitive element 113/213. According to the illustrated embodiment, when a force is applied, per arrows F, to a member 36, which is shown mounted over thermoplastic adhesive member 35, in conjunction with heating, as previously described, member 35 will deform to conform to fillet 32, for example, as illustrated in FIG. 3D, and thereby provide for additional electrical isolation to prevent arcing from one feedthrough member 107 to another (among unipolar assemblies 310' or within multipolar assembly 320').

FIG. 3D illustrates member 36 acting as a strain relief member to protect the joint between feedthrough member 107 and capacitive member 113/123 when feedthrough member 107 is subsequently bent, for example, via arrow B, in order to electrically connect member 107, for example, via wire bonding, parallel gap welding, or laser welding, to circuitry contained within device housing 905 (FIG. 1A). According to some alternate embodiments, strain relief member 36 doubles as a weighting member to apply the force to deform thermoplastic adhesive member 35, so that forces F need not be applied. According to yet further embodiments, a force may be applied directly to thermoplastic adhesive member 35, for example, via a weighting member applied directly onto member 35, and strain relief member 36 may, or may not, be subsequently mounted onto heat and pressure deformed member 35.

FIG. 4 is a section view through section line A-A of FIGS. 1A-B of yet another feedthrough assembly 410/420, according to additional embodiments of the present invention. (The item number 410 denotes a unipolar type, and 420, a multipolar type, for example, with reference to FIGS. 1B-C.) FIG. 4 illustrates assembly 410/420 including insulator element 25, capacitive element 113/213, conductive material 111/121, and heat and pressure deformed thermoplastic adhesive member 34, similar to assembly 310/320 of FIG. 3B, wherein member 34 isolates conductive material 112/122 from joints 250 of insulator element 25. FIG. 4 further illustrates assembly 410/420 including an alumina substrate 42 extending around feedthrough member 107, having been inserted between divider 202 and thermoplastic adhesive member 34. According to the illustrated embodiment, substrate 42 provides added rigidity to divider 202 so that loading (per arrows F shown in FIG. 3A) may be increased to achieve a greater compressive force, and thus a greater deformation of member 34, between divider 202, for example, formed from polyimide, and capacitive element 113/123. If divider 202 is sufficiently rigid, for example, being formed itself from alumina, substrate 42 may be omitted, for example, as in the previously presented assemblies 310/320 and 310'/320'. It should be noted that assembly 410/420 may further include either or both of thermoplastic adhesive member 35 and strain relief member 36, as in assembly 310'/320' of FIG. 3D.

As previously noted, implementation of the above-described method for capacitor attachment prevents undesired wicking of non-conductive epoxy in the capacitor hole. Additionally, optimal filling of conductive adhesive is achieved in the capacitor hole. With known volume available for dispensing in the capacitor hole, the process can be fully automated for epoxy dispensing. Moreover, with an optimal filling of conductive adhesive in the capacitors, the resulting equivalent series resistance can be lowered and improved EMI filtering characteristics can be achieved. Product reliability is also greatly improved (30-40%) because of the optimal filling of conductive adhesive in the capacitors. Undesired flow of the non-conductive epoxy in the brazed joint can be prevented, thus allowing the feedthrough to be leak tested. Additionally, since the non-conductive epoxy is entirely contained in the gap between the polyimide preform and the capacitor bottom surface, the exact volume of the non-conductive epoxy preform can be calculated to seal the bottom of the capacitor. With a known volume available under the capacitor, the process can be automated to dispense an exact amount of thixotropic non-conductive epoxy in the assembly. Thermoplastic adhesives bond in a few seconds compared to the thermosetting adhesives which may take a few hours to cure. Low elastic modulus reduces stress to the bonded capacitor. Thermoplastic adhesives could be stored at room temperature without degradation in properties. Piece parts are reduced in the assembly process of filtered feedthroughs. Low cost in production and/or components is achieved. The process could be combined with solder reflow process, thereby reducing cycle time for processing these feedthroughs.

In the foregoing detailed description, the invention has been described with reference to specific embodiments. However, it may be appreciated that various modifications and changes can be made without departing from the scope of the invention as set forth in the appended claims.

The invention claimed is:

1. A feedthrough assembly for an implantable medical device, the assembly comprising:
   a ferrule;
   a feedthrough member extending through the ferrule;
   an insulator element extending around a first portion of the feedthrough member within the ferrule;
   a hermetically sealing joint between the feedthrough member and the insulator element;
   a capacitive element extending around a second portion of the feedthrough member within the ferrule, the capacitive element including a first external surface facing the insulator element and extending laterally from the feedthrough member toward the ferrule, and a second external surface, opposite the first external surface, extending laterally from the feedthrough member toward the ferrule;
   a conductive material extending between the feedthrough member and the capacitive element and between the ferrule and the capacitive element, the conductive material electrically coupling the feedthrough member and the ferrule to the capacitive element; and
   a heat and pressure deformed thermoplastic adhesive member extending around the feedthrough member, within the ferrule, to isolate the conductive material, the adhesive member being sealed against the first external surface of the capacitive element and being spaced apart from the hermetically sealing joint.

2. The assembly of claim 1, further comprising a non-conductive divider extending within the ferrule between the hermetically sealing joint and the adhesive member.

3. The assembly of claim 2, further comprising an alumina washer extending around the feedthrough member within the ferrule, the alumina washer being located between the divider and the adhesive member.

4. The assembly of claim 1, wherein:
   the conductive material extends in a fillet around the feedthrough member adjacent to the second external surface of the capacitive element; and
   further comprising another heat and pressure deformed thermoplastic adhesive member extending over the fillet of the conductive material to further isolate the conductive material.

5. The assembly of claim 4, further comprising a strain relief member extending around the feedthrough member such that the other adhesive member is located between the strain relief member and the fillet of the conductive material.

6. The assembly of claim 1, wherein the heat and pressure deformed thermoplastic adhesive member comprises a material selected from the group consisting of: polysulfone, phenoxy and PEEK.

7. An implantable medical device comprising a feedthrough assembly, the feedthrough assembly comprising:
   a ferrule;
   a feedthrough member extending through the ferrule;
   an insulator element extending around a first portion of the feedthrough member within the ferrule;
   a hermetically sealing joint between the feedthrough member and the insulator element;
   a capacitive element extending around a second portion of the feedthrough member within the ferrule, the capacitive element including a first external surface facing the insulator element and extending laterally from the feedthrough member toward the ferrule, and a second external surface, opposite the first external surface, extending laterally from the feedthrough member toward the ferrule;
   a conductive material extending between the feedthrough member and the capacitive element and between the ferrule and the capacitive element, the conductive material electrically coupling the feedthrough member and the ferrule to the capacitive element; and
   a heat and pressure deformed thermoplastic adhesive member extending around the feedthrough member, within the ferrule, to isolate the conductive material, the adhesive member being sealed against the first external surface of the capacitive element and being spaced apart from the hermetically sealing joint.

8. The device of claim 7, wherein the feedthrough assembly further comprises a non-conductive divider extending within the ferrule between the hermetically sealing joint and the adhesive member.

9. The device of claim 8, wherein the feedthrough assembly further comprises an alumina washer extending around the feedthrough member within the ferrule, the alumina washer being located between the divider and the adhesive member.

10. The device of claim 7, wherein:
the conductive material of the feedthrough assembly extends in a fillet around the feedthrough member adjacent to the second external surface of the capacitive element; and
the feedthrough assembly further comprises another heat and pressure deformed thermoplastic adhesive member extending over the fillet of the conductive material to further isolate the conductive material.

11. The device of claim 10, wherein the feedthrough assembly further comprises a strain relief member extending around the feedthrough member such that the other adhesive member is located between the strain relief member and the fillet of the conductive material.

12. The device of claim 7, wherein the heat and pressure deformed thermoplastic adhesive member of the feedthrough assembly comprises a material selected from the group consisting of: polysulfone, phenoxy and PEEK.

13. A method for manufacturing a feedthrough assembly for an implantable medical device, the method comprising:
hermetically sealing an insulator element to a feedthrough member and to a ferrule, the insulator element extending around the feedthrough member within the ferrule;
mounting a divider around the feedthrough member within the ferrule adjacent to the insulator element;
mounting a thermoplastic adhesive member around the feedthrough member within the ferrule, adjacent to the divider, on an opposite side of the divider from the insulator element;
mounting a capacitive element around the feedthrough member and within the ferrule, such that a first external surface of the capacitive element abuts the adhesive member;
pressing the mounted capacitive element against the mounted thermoplastic adhesive member, while heating the mounted thermoplastic adhesive member, in order to deform the thermoplastic adhesive member and thereby form a seal between the capacitive element and the thermoplastic adhesive member; and
coupling the mounted capacitive element to the feedthrough member and to the ferrule by backfilling an area between the capacitive element and the feedthrough member, and an area between the capacitive element and the ferrule, with a conductive material.

14. The method of claim 13, wherein pressing the mounted capacitive element against the mounted thermoplastic adhesive member comprises mounting a weighting member onto a second external surface of the capacitive element, the second external surface being opposite the first external surface.

15. The method of claim 13, further comprising mounting an alumina washer around the feedthrough member within the ferrule, against the divider, prior to mounting the thermoplastic adhesive member, the mounted alumina washer being located between the adhesive member and the divider.

16. The method of claim 13, wherein backfilling the area between the capacitive element and the feedthrough member comprises forming a fillet around the feedthrough member adjacent to a second external surface of the capacitive element, the second external surface being opposite the first external surface; and further comprising:
mounting another thermoplastic adhesive member around the feedthrough member such that the fillet is located between the capacitive element and the other adhesive member; and
pressing the other mounted thermoplastic adhesive member against the fillet, while heating the assembly, in order to deform the other thermoplastic adhesive member and thereby form a seal between the other thermoplastic adhesive member and the fillet.

17. The method of claim 16, wherein pressing the other mounted thermoplastic adhesive member against the fillet comprises mounting a weighting member onto the other mounted thermoplastic adhesive member.

18. The method of claim 17, wherein the weighting member is mounted around the feedthrough member and the weighting member comprises a strain-relief member for the feedthrough member.

19. The method of claim 16, further comprising mounting a strain relief member over the other mounted thermoplastic adhesive member.

20. The method of claim 19, wherein mounting the strain relief member is performed prior to pressing the other mounted thermoplastic adhesive member against the fillet.

* * * * *